United States Patent
Hachisuka et al.

(10) Patent No.: US 9,465,978 B2
(45) Date of Patent: Oct. 11, 2016

(54) FEELING MONITORING SYSTEM

(71) Applicant: DENSO CORPORATION, Kariya, Aichi-pref. (JP)

(72) Inventors: Satori Hachisuka, Nagoya (JP); Satoshi Nozoe, Chiryu (JP); Takeshi Enya, Nagoya (JP); Makoto Sakai, Nishikasugai-gun (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/390,806

(22) PCT Filed: Apr. 4, 2013

(86) PCT No.: PCT/JP2013/002333
§ 371 (c)(1),
(2) Date: Oct. 6, 2014

(87) PCT Pub. No.: WO2013/153781
PCT Pub. Date: Oct. 17, 2013

(65) Prior Publication Data
US 2015/0078632 A1 Mar. 19, 2015

(30) Foreign Application Priority Data
Apr. 10, 2012 (JP) ................. 2012-089493

(51) Int. Cl.
| G06K 9/00 | (2006.01) |
| A61B 5/16 | (2006.01) |
| A61B 5/18 | (2006.01) |
| G06K 9/78 | (2006.01) |
| A61B 5/00 | (2006.01) |

(52) U.S. Cl.
CPC ......... *G06K 9/00308* (2013.01); *A61B 5/0077* (2013.01); *A61B 5/165* (2013.01); *A61B 5/18* (2013.01); *A61B 5/742* (2013.01); *A61B 5/743* (2013.01); *A61B 5/7405* (2013.01); *G06K 9/00832* (2013.01); *G06K 9/78* (2013.01); *A61B 5/7415* (2013.01); *A61B 2576/02* (2013.01)

(58) Field of Classification Search
None
See application file for complete search history.

(56) References Cited

FOREIGN PATENT DOCUMENTS

| JP | 2003-339681 A | 12/2003 |
| JP | 2003339681 A | * 12/2003 |
| JP | 2010-092094 A | 4/2010 |
| JP | 2010-226484 A | 10/2010 |
| JP | 2011-117905 A | 6/2011 |

OTHER PUBLICATIONS

International Search Report and Written Opinion of the International Searching Authority mailed May 21, 2013 for the corresponding International application No. PCT/JP2013/002333 (and English translation).
Paul Ekman and Erika L. Rosenberg. "What the Face Reveals Basic and Applied Studies of Spontaneous Expression Using the Facial Action Coding System (FACS)." Second Edition, Oxford University Press, 2005, pp. 11-18.
Office Action mailed Sep. 2, 2014 issued in corresponding JP patent application No. 2012-089493 (and English translation).
Office Action issued Sep. 2, 2015 in the corresponding CN application No. 201380019356.3 (English translation only).

* cited by examiner

*Primary Examiner* — Kim Vu
*Assistant Examiner* — Fred Hu
(74) *Attorney, Agent, or Firm* — Posz Law Group, PLC (57) ABSTRACT

A feeling monitoring system includes a facial image acquisition portion, a feeling information acquisition section, and a feeling display generation section. The facial image acquisition portion is capable of acquiring a facial image of an occupant individually sitting in each seating position of two or more seating positions in a vehicle. The feeling information acquisition section acquires feeling information representing the feeling of the occupant based on the facial image acquired from the facial image acquisition portion. The feeling display generation section generates a feeling display corresponding to the feeling information acquired by the feeling information acquisition section.

20 Claims, 8 Drawing Sheets

FEELING MONITORING SYSTEM

CROSS REFERENCE TO RELATED APPLICATION

This application is a U.S. national stage application of PCT/JP2013/002333 filed on Apr. 4, 2013 and is based on Japanese Patent Application No. 2012-89493 filed on Apr. 10, 2012, the disclosures disclosure of which are incorporated herein by reference.

TECHNICAL FIELD

The present disclosure relates to a feeling monitoring system.

BACKGROUND ART

Patent Literature 1 discloses such a technology as described below. The facial expressions of multiple occupants in a vehicle are acquired; and the degree of favorableness of the facial expression of each occupant are learned in connection with the vehicle exterior environment and detected on the time series. Then such a driving route (vehicle exterior environment) as to keep the facial expressions of the occupants favorable is proposed.

PRIOR ART LITERATURES

Patent Literature

Patent Literature 1: JP 2011-117905 A

SUMMARY OF INVENTION

In the technology described in Patent Literature 1, the information related to the facial expressions of occupants is used only in route selection assisting processing and is not displayed. Therefore, each occupant cannot learn other occupants' feelings. The present disclosure is made in consideration of the foregoing and it is an object thereof to provide a feeling monitoring system that makes it possible for each occupant to learn the feelings of other occupants.

A feeling monitoring system according to an aspect of the present disclosure includes: a facial image acquisition portion capable of acquiring a facial image of an occupant individually sitting in each seating position of two or more seating positions of a vehicle; a feeling information acquisition section acquiring feeling information representing feeling of the occupant based on the facial image acquired by the facial image acquisition portion; and a feeling display generation section generating feeling display corresponding to the feeling information acquired by the feeling information acquisition section.

For example, when there are multiple occupants in a vehicle, the feeling monitoring system according to the present aspect is capable of generating a feeling display representing the feeling of each occupant. For this reason, even though an occupant is sitting in a position where he/she cannot directly see another occupant, he/she can readily become aware of an unusual change or the like of that occupant.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

1. Configuration of Feeling Monitoring System 1

Figure 1:
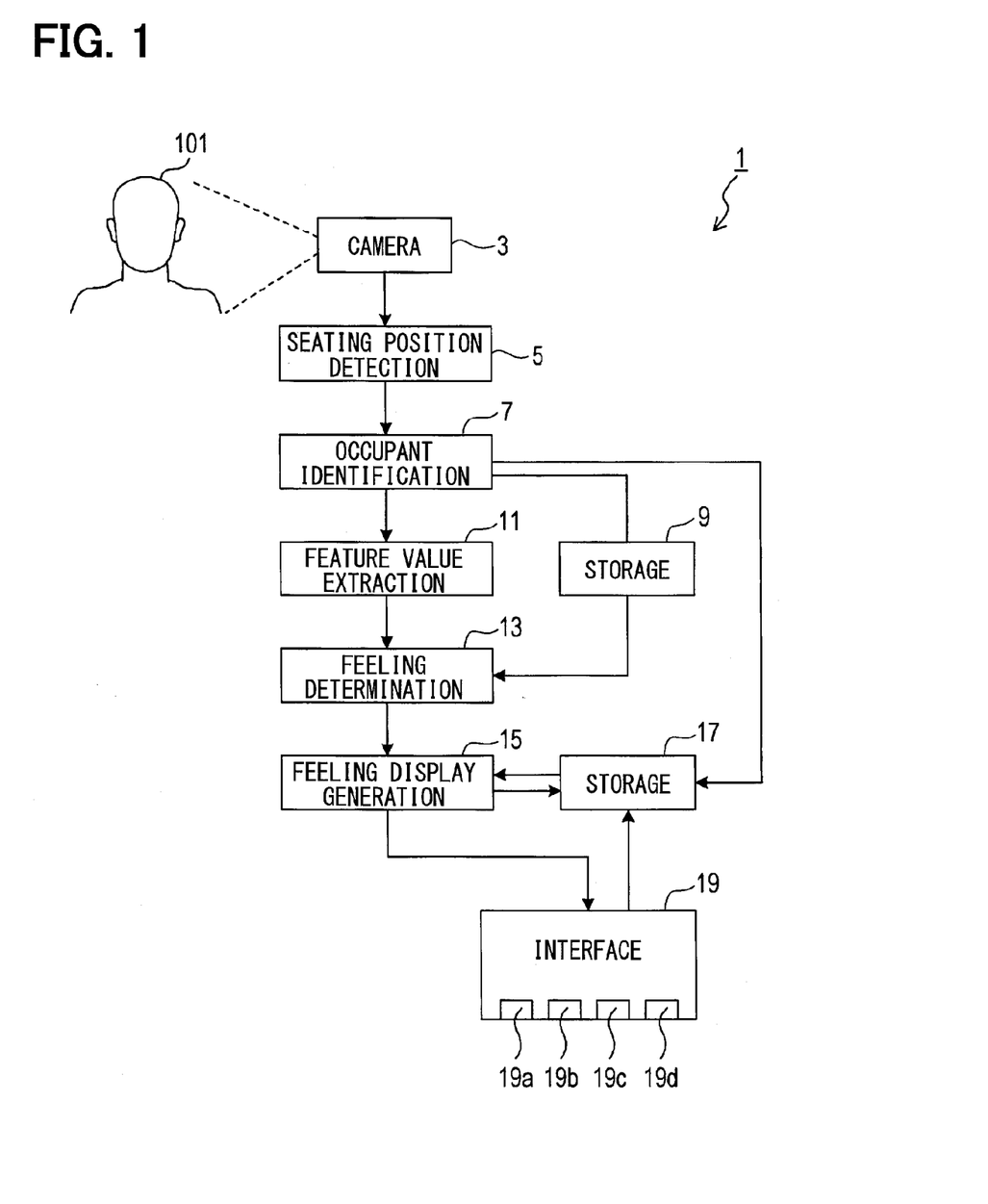
FIG. 1 is a block diagram representing a configuration of a feeling monitoring system.

A description will be given to a configuration of a feeling monitoring system 1 with reference to FIG. 1. The feeling monitoring system 1 is an in-vehicle system mounted in a vehicle and includes: a camera (facial image acquisition portion) 3; a seating position detection section 5; an occupant identification section 7; a storage portion 9; a feature value extraction section 11; a feeling determination section (feeling information acquisition section) 13; a feeling display generation section 15; a storage portion (first storage portion, second storage portion) 17; and an interface portion 19. The seating position detection section 5, occupant identification section 7, feature value extraction section 11, feeling determination section 13, and feeling display generation section 15 are formed of a publicly known computer.

The camera 3 is installed on the ceiling of the vehicle compartment and the coverage of its imaging includes all the seating positions (driver's seat, passenger seat, right rear seat, left rear seat, etc.) in the vehicle compartment. Therefore, the camera 3 is capable of picking up the images of the face and body of the occupant 101 individually sitting in every seating position in the vehicle compartment. The camera 3 may be provided for each seating position. In this case, each camera 3 picks up the image of the face and body of one occupant 101 sitting in the seating position corresponding thereto. As the camera 3, a camera for picking up the image of the front area (driver's seat and passenger seat) in the vehicle compartment and a camera for picking up the image of the rear area (rear seats) in the vehicle compartment may be installed.

The seating position detection section 5 detects the seating position of an occupant 101 from an image picked up by the camera 3. That is, it determines whether or not an occupant 101 is sitting in each seating position by image recognition in an image picked up by the camera 3.

The occupant identification section 7 identifies each occupant 101 using an image picked up by the camera 3. Details will be described later.

The storage portion 9 holds identifiers for identifying occupants 101. The identifier is features, which are specific to each occupant and can be extracted from images by image recognition. Examples of the identifier include the pattern (the shape and size of facial parts such as eyes, nose, mouth, and the like, the positional relation between facial parts, and the like) of a face, the shape and color of clothing, the shape of a body, and the like. The storage portion 9 holds the identifiers of occupants 101 cataloged in the past on an occupant-by-occupant basis. In the storage portion 9, seating positions, feeling informations, described later, and the names of occupants, and the like can be stored in connection with the identifiers. The storage portion 9 also stores a database referenced to by the feeling determination section 13 to determine feeling.

It is noted that in the present application, "information" may be used as being countable noun as well as uncountable noun.

The feature value extraction section 11 recognizes the face of an occupant 101 from an image picked up by the camera 3 and extracts preset feature values (AU) in the face by image processing. When it recognizes the faces of multiple occupants 101 in an image picked up by the camera 3, it extracts feature values (AU) with respect to each occupant. The details of extraction of feature values will be described later.

The feeling determination section 13 determines the feeling of an occupant 101 from the feature values (AU) extracted by the feature value extraction section 11 and generates feeling information. When it recognizes the faces of multiple occupants 101 in an image picked up by the camera 3, it generates feeling information with respect to each occupant. The details of generation of feeling information will be described later.

The feeling display generation section 15 generates a feeling display using the feeling information generated by the feeling determination section 13. The feeling display generation section 15 also generates a notification sound. The details of generation of feeling display and notification sound will be described later.

The storage portion 17 holds a map used by the feeling display generation section 15 to generate a feeling display and a notification sound. (The map includes a basis related to the type of feeling information and the correspondence between the intensity of a feeling and the mode of a feeling display.) There are two types of the map: (i) a map stored for each occupant 101 and related to the identifier of the occupant 101 and (ii) a versatile map. The contents of maps will be described in detail later.

The interface portion 19 includes: a display portion 19*a* capable of displaying an image, a speaker 19*b* capable of outputting a sound, a microphone 19*c* capable of inputting a sound, and a manipulation portion (keyboard, various switches, touch panel, and the like) 19*d* accepting input manipulation by an occupant 101. The interface portion 19 shows a feeling display generated by the feeling display generation section 15 on the display portion 19*a*. A notification sound generated by the feeling display generation section 15 is given off by the speaker 19*b*. The maps stored in the storage portion 17 can be edited through voice input to the microphone 19*c* or input manipulation with the manipulation portion 19*d*. (The editing includes adding a new map, adding or rewriting the contents of an existing map, and deleting a map, and the like.)

The display portion 19*a* of the interface portion 19 may be viewable to the driver of a vehicle (for example, it may be difficult for other occupants to view or be unviewable to them). Examples of such a display portion 19*a* include meter display screen, dual display screen of car navigation system, and the like. The display portion 19*a* may be viewable to some or all of the occupants other than the driver (for example, it may be difficult for the driver to view or be unviewable to him/her). An example of such a display portion 19*a* is a display portion provided on the back side of a seat or the ceiling. Or, the display portion 19*a* may be viewable both to the driver and to the other occupants.

2. Processing Carried Out by Feeling Monitoring System 1

A description will be given to processing carried out by the feeling monitoring system 1 with reference to FIG. 2 to FIG. 8.

It is noted that a flowchart or the processing of the flowchart in the present application includes sections (also referred to as steps), each of which is represented, for instance, as S1. Further, each section can be divided into several sub-sections while several sections can be combined into a single section. Furthermore, each of thus configured sections can be also referred to as a device, module, or means.

Figure 2:
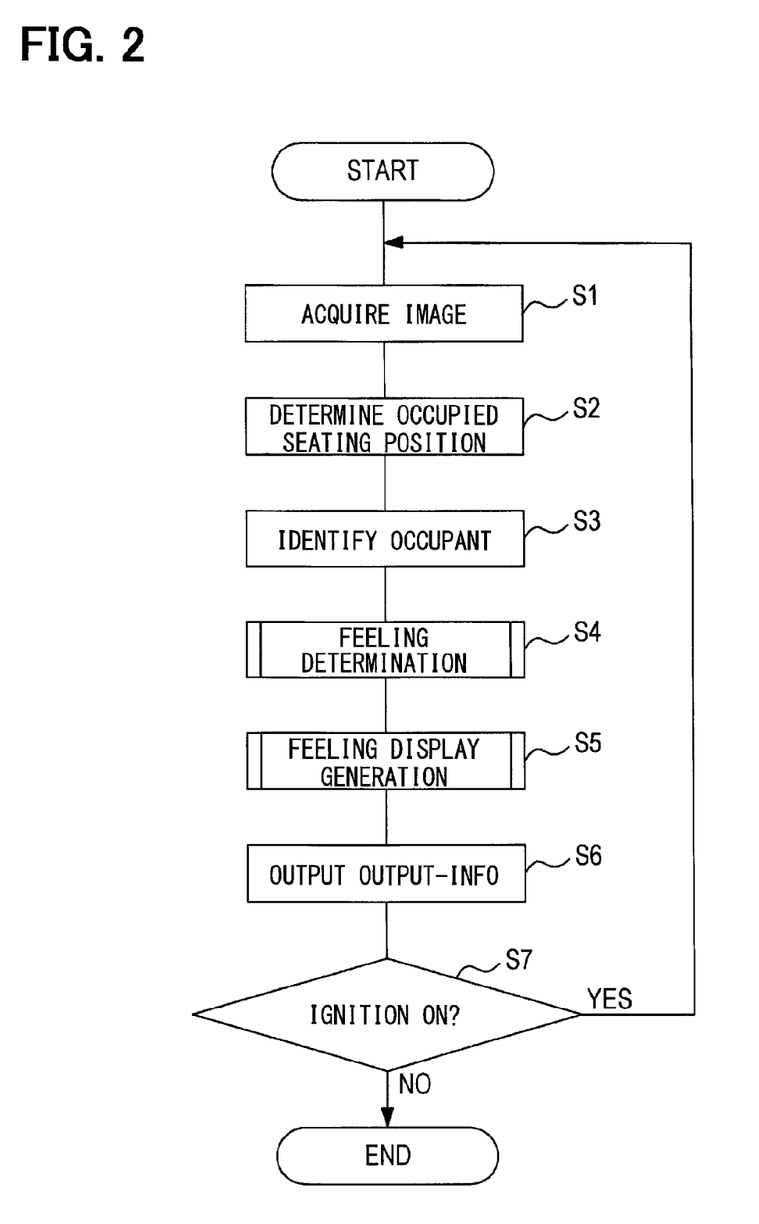
FIG. 2 is a flowchart showing main processing carried out by a feeling monitoring system.

The feeling monitoring system 1 repeatedly carries out the respective processing shown in FIG. 2 at predetermined time intervals while the ignition of the vehicle mounted therewith is ON. At S1 in FIG. 2, the camera 3 acquires an image of the area embracing all the seating positions in the vehicle. When an occupant is sitting in any seating position in the vehicle, the face and body of the occupant are included in this image. When respective occupants are individually sitting in two or more seating positions in the vehicle, the faces and bodies of all the occupants are included in this image.

At S2, the seating position detection section 5 analyzes the image acquired at S1 and thereby determines whether or not an occupant is sitting in each seating position in the vehicle.

At S3, the occupant identification section 7 carries out identification of the sitting occupants in all the seating positions determined to be occupied by an occupant at S2 as described below. First, with respect to one seating position α determined to be occupied by an occupant at S2, the identifier of the occupant sitting in the seating position α is extracted using the image acquired at S1. The extracted identifier is compared with the identifiers already stored in the storage portion 9. When the result of the comparison indicates that the identifiers stored in the storage portion 9 include an identifier identical with or similar to the identifier of the occupant sitting in the seating position α, that identifier is stored in the storage portion 9 in connection with the seating position α. When the identifiers stored in the storage portion 9 do not include an identifier identical with or similar to the identifier of the occupant sitting in the seating position α, the identifier of the occupant sitting in the seating position α is newly stored in the storage portion 9 in connection with the seating position α.

The above-described processing is similarly carried out with respect to not only the seating position α but also all the seating position β, γ . . . determined to be occupied by an occupant at S2.

At S4, feeling determination processing is carried out to acquire feeling information representing the feeling of an occupant in a seating position determined to be occupied by the occupant at S2. When there are multiple seating positions determined to be occupied by occupants at S2, occupant feeling information is acquired in each of all the seating positions.

Figure 3:
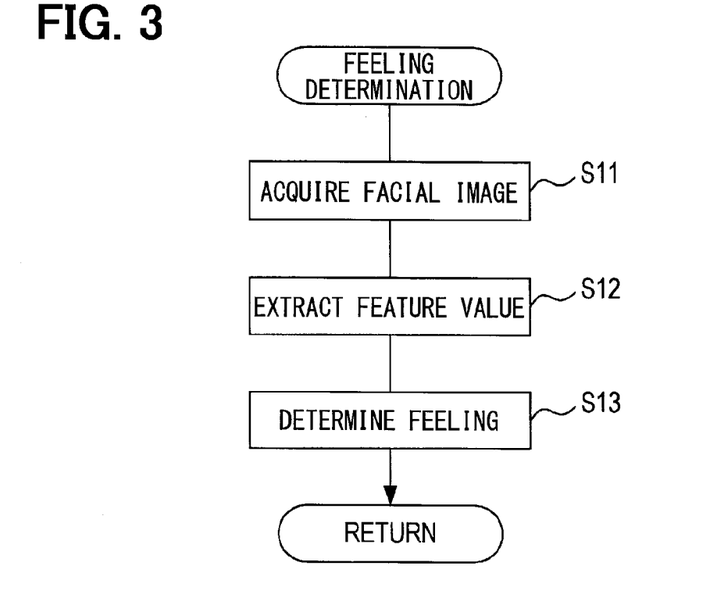
FIG. 3 is a flowchart showing feeling determination processing carried out by a feeling monitoring system.

This feeling determination processing will be described with reference to FIG. 3. At S11 in FIG. 3, an image embracing all the seating positions in the vehicle compartment is repeatedly acquired from the camera 3 at predetermined time intervals.

At S12, an image analysis is carried out by the feature value extraction section 11 with respect to each of the images (facial images including the faces of occupants) repeatedly acquired at S11. The features (for example, eyebrow, eyelid, mouth) of the face of an occupant are extracted and the movement of the features (hereafter, referred to as AU (Action Unit)) with the passage of time are extracted. Examples of AU are listed in Table 1 and FIG. 5. R and L in FIG. 5 denote the right and left of a face.

TABLE 1

| AU | Facial Expressions |
|---|---|
| 1 | Raising inner part of eyebrow |
| 2 | Raising outer part of eyebrow |
| 4 | Lowering eyebrow |
| 5 | Raising upper eyelid |
| 6 | Raising cheek |
| 7 | Rigidifying eyelid |
| 8 | Drawing lips |
| 9 | Wrinkles on nose |
| 10 | Raising upper lip |
| 11 | Wrinkles under nose |
| 12 | Raising corner of mouth |
| 13 | Thin lips |
| 14 | Dimple |
| 15 | Lowering corner of mouth |
| 16 | Lowering lower lip |
| 17 | Raising chin |
| 18 | Wrinkles on lips |
| 19 | Slightly opening mouth |
| 20 | Expanding lips |
| 22 | Funnel-shaped lips |
| 23 | Firmly closing mouth |
| 24 | Pout out lips |
| 25 | Open mouth |
| 26 | Lowering chin |
| 27 | Largely opening mouth |
| 28 | Sucking lips |
| 30 | Horizontally moving chin |
| 32 | Bite |
| 38 | Flaring nostrils |
| 39 | Narrowing nostrils |
| 45 | Blinking |

It is known that there is correlation between human feelings and AU (Facial Action Coding System espoused by Ekman).

At S13, the feeling determination section 13 determines the feeling of an occupant from AU extracted at S12. Specifically, the following processing is carried out. The storage portion 9 holds a database indicating the correspondence between AU and feelings. The database holds the following correspondence, for example.

Pleasure: 6R, 6L, 12R, 12L, 25
Astonishment: 1R, 1L, 2R, 2L, 5R, 5L, 25, 27
Grief: 1R, 1L, 4R, 4L, 15R, 15L, 17

The type (pleasure, grief, and the like) of the feeling of an occupant can be determined by applying AU extracted at S12 to this database. The intensity of the feeling can be determined from the magnitude of AU. Information including the type of feeling and the intensity of feeling will be designated as feeling information. Feeling information is generated with respect to all the seating positions determined to be occupied by the occupants at S2. Feeling informations are stored in the storage portion 9 in connection with the seating positions and identifiers corresponding thereto. For example, the feeling information pertaining to an occupant (whose identifier will be designated as identifier X) sitting in seating position α is stored in the storage portion 9 in connection with seating position α and identifier X. As described above, the feature value extraction section 11 acquires feeling information representing the feeling of an occupant based on a facial image acquired from the camera 3.

The description will be back to FIG. 2. At S5, the feeling display generation section 15 carries out feeling display generation processing to generate a feeling display corresponding to the feeling information acquired at S4. This feeling display generation processing will be described with reference to FIG. 4. At S21 in FIG. 4, the feeling information stored in the storage portion 9 at S13 is invoked. When there are multiple feeling informations, all of them are invoked.

Figure 4:
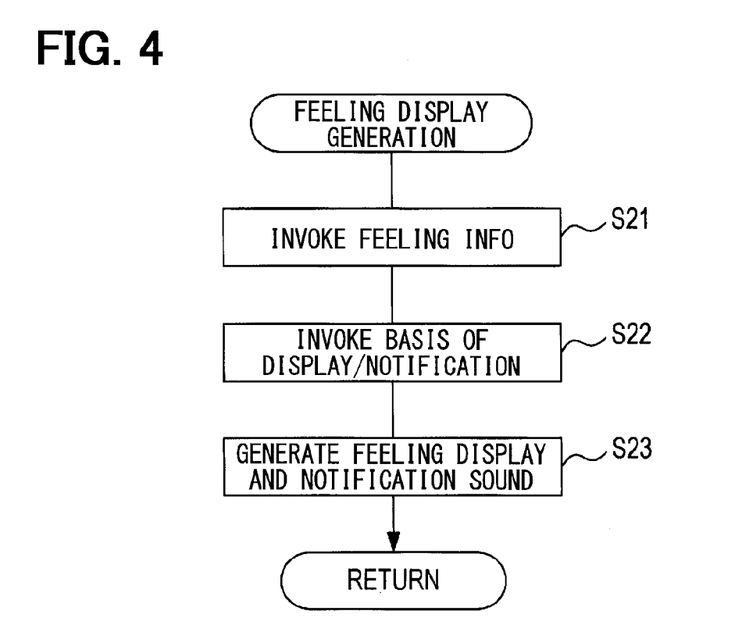
FIG. 4 is a flowchart showing feeling display generation processing carried out by a feeling monitoring system.
Figure 5:
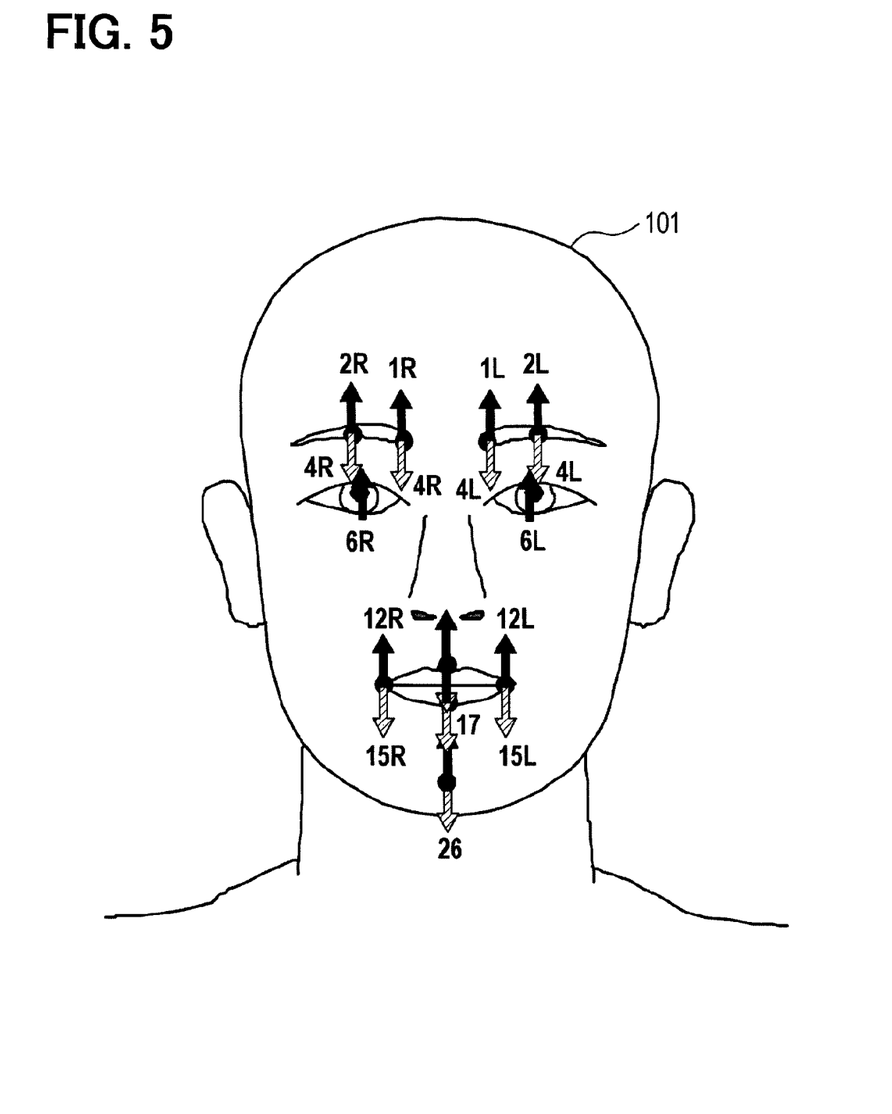
FIG. 5 is an explanatory drawing showing AU (Action Unit) in the face of an occupant.

At S22, a map is invoked from the storage portion 17. Specifically, the processing described below is carried out. First, the following processing is carried out with respect to one seating position α determined to be occupied by an occupant at S2: the identifier stored in connection with seating position α is read from the storage portion 9. A map related to the read identifier is searched for in the storage portion 17 and when there is a map related thereto, the map is read. When there is not a map related thereto, a versatile map is read. When aside from seating position α, there is a seating position determined to be occupied by an occupant at S2, a map is similarly read also with respect to all the seating positions other than seating position α.

The map cited here is as indicated by Table 2 to Table 4.

TABLE 2

| Map for Occupant (Identifier X) | | | | |
|---|---|---|---|---|
| Type of feeling | Generation of feeling display | Display color | Lighting or blinking | Notification sound |
| Smile (pleasure) | ○ | Pink | Lighting for L5 or below, blinking for L6 or above | L6 or above |
| Anger (irritation) | ○ | Red | Lighting for L5 or below, blinking for L6 or above | L6 or above |
| Astonishment (close call) | ○ | Blue | Lighting for L5 or below, blinking for L6 or above- | L6 or above |
| Grief (tear-stained face) | X | — | — | — |
| Tedium | ○ | Green | Lighting for L5 or below, blinking for L6 or above | L6 or above |
| Embarrassment | X | — | — | — |
| Drowsiness | ○ | Purple | Lighting for L5 or below, blinking for L6 or above | L6 or above |

TABLE 3

| Map for Occupant (Identifier Y) | | | | |
|---|---|---|---|---|
| Type of feeling | Generation of feeling display | Display color | Lighting or blinking | Notification sound |
| Smile (pleasure) | ○ | Pink | Lighting for L6 or below, blinking for L7 or above | L8 or above |
| Anger (irritation) | ○ | Red | Lighting for L6 or below, blinking for L7 or above | L8 or above |

TABLE 3-continued

Map for Occupant (Identifier Y)

| Type of feeling | Generation of feeling display | Display color | Lighting or blinking | Notification sound |
|---|---|---|---|---|
| Astonishment (close call) | O | Blue | Lighting for L6 or below, blinking for L7 or above | L8 or above |
| Grief (tear-stained face) | O | Orange | Lighting for L6 or below, blinking for L7 or above | L8 or above |
| Tedium | O | Green | Lighting for L6 or below, blinking for L7 or above | L8 or above |
| Embarrassment | O | Yellow | Lighting for L6 or below, blinking for L7 or above | L8 or above |
| Drowsiness | O | Purple | Lighting for L6 or below, blinking for L7 or above | L8 or above |

TABLE 4

Versatile Map

| Type of feeling | Generation of feeling display | Display color | Lighting or blinking | Notification sound |
|---|---|---|---|---|
| Smile (pleasure) | O | Pink | Lighting for L7 or below, blinking for L8 or above | L8 or above |
| Anger (irritation) | O | Red | Lighting for L7 or below, blinking for L8 or above | L8 or above |
| Astonishment (close call) | X | — | — | — |
| Grief (tear-stained face) | X | — | — | — |
| Tedium | X | — | — | — |
| Embarrassment | X | — | — | — |
| Drowsiness | O | Purple | Lighting for L7 or below, blinking for L8 or above | L8 or above |

The map in Table 2 is related to identifier X; the map in Table 3 is related to identifier Y different from identifier X; and the map in Table 4 is a versatile map that is not related to any identifier.

Each map includes a basis pertaining to the type of feeling information for which a feeling display should be generated. That is, each map defines the feeling information as follows: feeling information containing some types of feeling of all the types of feeling is feeling information for which a feeling display is to be generated; and feeling information containing the other types of feeling is feeling information for which a feeling display is not to be generated (the column of "Generation of feeling display" in Tables 2 to 4). The contents of the column of "Generation of feeling display" may be different from map to map (that is, from identifier to identifier) or may be common to all the maps.

An example will be taken. In the column of "Generation of feeling display" in the map in Table 2, Smile (pleasure), Anger (irritation), Astonishment (close call), Tedium, and Drowsiness are marked with "O." Feeling information containing any of these types of feeling is taken as feeling information for which a feeling display is to be generated. In the column of "Generation of feeling display", Grief (tear-stained face) and Embarrassment are marked with "X." Feeling information containing either of these types of feeling is taken as feeling information for which a feeling display is not to be generated. This is the same with the maps in Table 3 and Table 4.

Each map defines the mode of each feeling display (display color, lighting or blinking). In each map, the column of "Display color" defines the color of feeling display with respect to each type of feeling in feeling information; and the column of "Lighting or blinking" defines the relation between the intensity of feeling in feeling information and the mode of feeling display, lighting or blinking. (The intensity of feeling is represented in 10 levels, L1 to L10 and a larger numerical value represents more intensified feeling.) An example will be taken. In the map in Table 2, the feeling display is defined as follows: the color of a feeling display generated based on feeling information in which the type of feeling is Smile (pleasure) is pink; and a feeling display lights up (brightness is constant) within the range of feeling intensity of L1 to L5 and blinks within the range of L6 to L10. This is the same with the maps in Table 3 and Table 4.

At S23, a feeling display and a notification sound are generated as described below. With respect to one seating position α determined to be occupied by an occupant at S2, a feeling display is generated from the map read at S22 and the feeling information related to seating position α. For this purpose, first, it is determined whether or not the type of feeling in the feeling information is marked with "O" in the column of "Generation of feeling display" in the map. (That is, it determined whether or not it agrees with the basis pertaining to the type of feeling information.) When the type of feeling is marked with "O," a feeling display is generated with respect to that feeling information. When the type of feeling is marked with "X," a feeling display is not generated with respect to that feeling information.

When a feeling display is generated, the design of the feeling display is determined according to the type of feeling in the feeling information. The type of feeling and the design of feeling display are related to each other in advance and stored in the storage portion 17. Some examples will be taken. When the type of feeling is Smile (pleasure), the design of the feeling display is as shown as feeling display 217 in FIG. 6; when the type of feeling is Anger (irritation), the design of the feeling display is as shown as feeling display 219 in FIG. 6; and when the type of feeling is Drowsiness, the design of the feeling display is as shown as feeling display 221 in FIG. 6. When a feeling display is generated, the color of the feeling display is determined based on the map and the mode of lighting/blinking (mode of feeling display) is determined according to the intensity of feeling in the feeling information.

When a feeling display is generated with respect to seating position α, the place where the feeling display is to be shown is determined based on the location of seating position α in the vehicle compartment. Specifically, when the seating position α is driver's seat, the location corresponding to the driver's seat is taken as the place of feeling display; when seating position α is passenger seat, the location corresponding to the passenger seat is taken as the place of feeling display; when seating position α is right rear seat, the location corresponding to the right rear seat is taken as the place of feeling display; and when seating position α is left rear seat, the location corresponding to the left rear seat is taken as the place of feeling display.

According to the foregoing, the feeling display (design, color, the mode of lighting/blinking) and the place thereof are determined with respect to seating position α. There may be a case where seating positions determined to be occupied by an occupant at S2 other than seating position α. In such a case, the processing to generate a feeling display and the place of the feeling display is similarly carried out also with respect to all the seating positions other than seating position α.

At S23, it is also determined according to feeling information whether to give off a notification sound. When feeling information for which a feeling display is to be generated contains any one type of feeling whose intensity meets the condition in the column of "Notification sound" in the map, it is determined that a notification sound should be given off. The notification sound may be made different according to the type of feeling meeting the condition in the column of "Notification sound." When feeling information for which a feeling display is to be generated does not contain at all the type of feeling whose intensity meets the condition of the column of "Notification sound" in the map, it is determined that a notification sound should not be given off. The type and volume of "notification sound" may be set according to the identifier of an occupant whose intensity of feeling meets the condition of the column of "Notification sound" in the map. Or, it may be determined according to the seating position of that occupant.

The description will be back to FIG. 2. At S6, the feeling display generation section 15 outputs a signal representing the contents (feeling display, the place thereof, whether to give off a notification sound) determined at S23 to the interface portion 19. When there are multiple feeling displays generated, all of them are outputted.

When there is a seating position determined not to be occupied by an occupant at S2, at S6, the positional information about that seating position is outputted to the interface portion 19. This positional information is used at the interface portion 19 to display the seating position not occupied by an occupant. When there is a seating position which was determined to be occupied by an occupant but for which a feeling display was determined not to be generated at S23, the positional information about that seating position is outputted to the interface portion 19. This positional information is used at the interface portion 19 to display the seating position which is occupied by an occupant but for which a feeling display is not generated.

Figure 6:
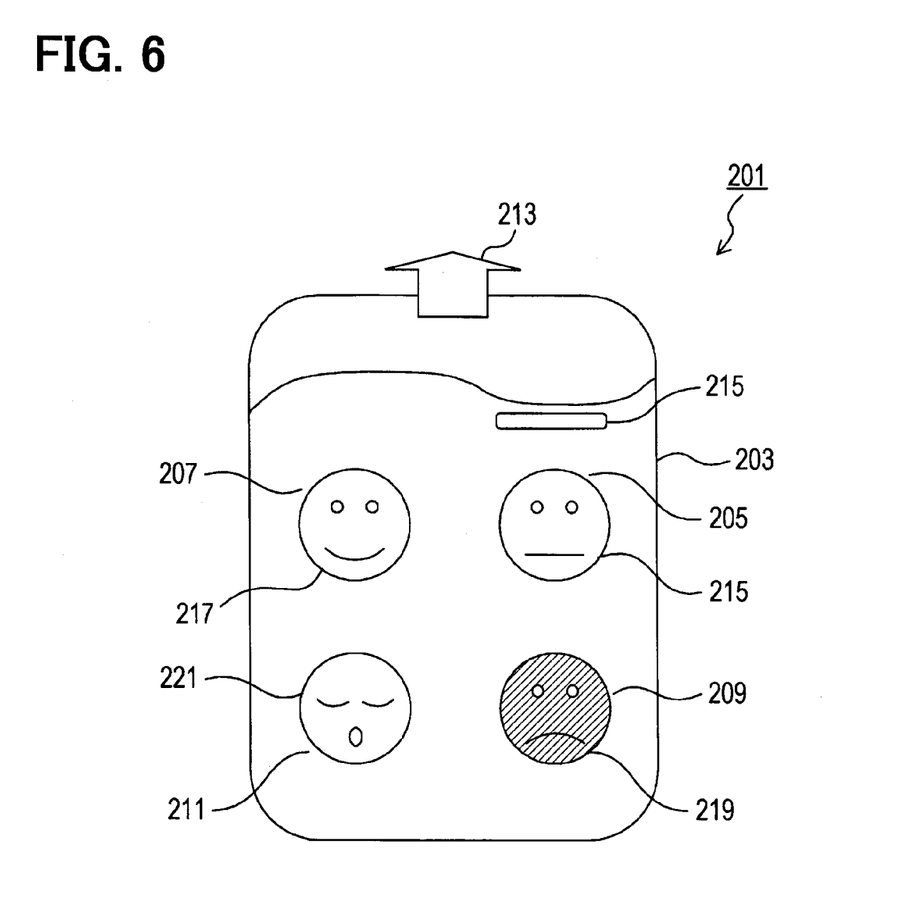
FIG. 6 is an explanatory drawing showing an example of a feeling display.

At the interface portion 19, the display or sound described below is given according to a signal inputted from the feeling display generation section 15. The display portion 19a of the interface portion 19 shows feeling displays 215, 217, 219, 221 as illustrated in, for example, FIG. 6. FIG. 6 illustrates an example of displays obtained when an occupant is detected in all the four seating positions and a feeling display is generated in all the seating positions.

The design, color, and mode of lighting/blinking of feeling displays 215, 217, 219, 221 are determined at S23. Feeling displays 215, 217, 219, 221 are shown in connection with the seating positions corresponding to the respective feeling displays based on the places of display determined at S23. An example will be given. Feeling display 215 is generated from the feeling information of the occupant (driver) sitting in the driver's seat among the seating positions. This feeling display 215 is shown in place 205 schematically representing the driver's seat. Similarly, feeling display 217 generated from the feeling information of the occupant sitting in the passenger seat is shown in place 207 schematically representing the passenger seat; feeling display 219 generated from the feeling information of the occupant sitting in the right rear seat is shown in place 209 schematically representing the right rear seat; and feeling display 221 generated from the feeling information of the occupant sitting in the left rear seat is shown in place 211 schematically representing the left rear seat.

The display portion 19a of the interface portion 19 expresses place 205 representing the driver's seat, place 207 representing the passenger seat, place 209 representing the right rear seat, and place 211 representing the left rear seat respectively by the following: line 203 representing the outline of the vehicle compartment; arrow 213 representing the traveling direction of the vehicle; symbol 215 representing the steering wheel; and the like.

Figure 7:
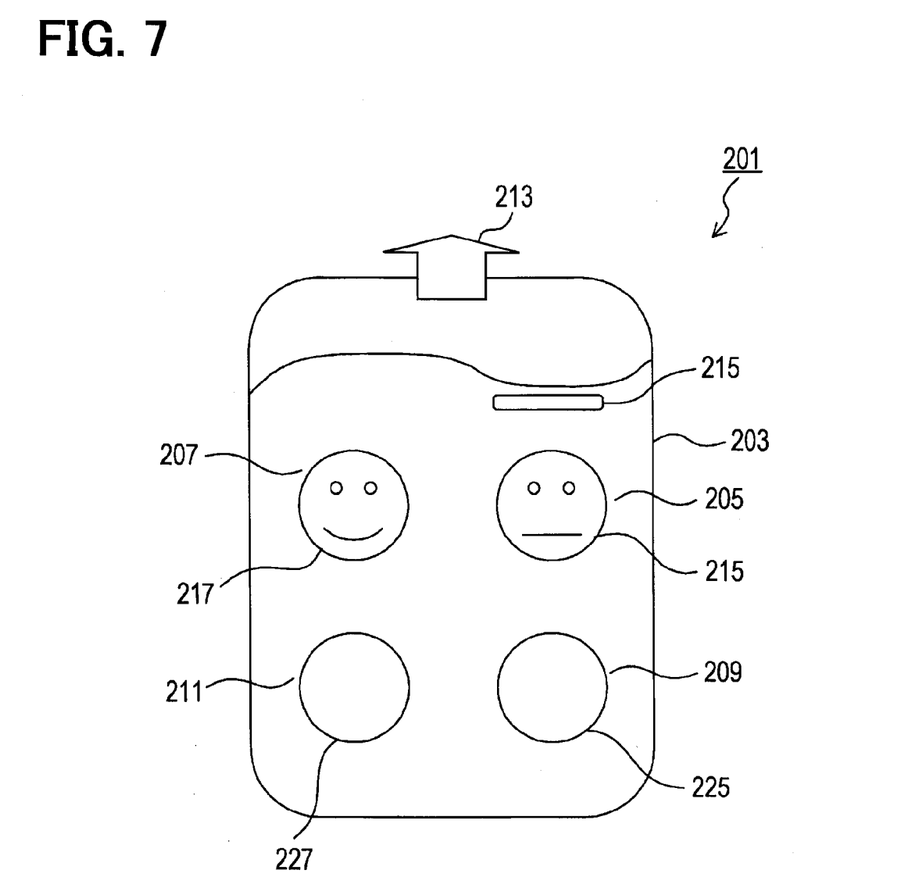
FIG. 7 is an explanatory drawing showing an example of a feeling display.

FIG. 7 shows an example of display shown in a case where although an occupant is detected in each of all the four seating positions, a feeling display is generated only in the driver's seat and the passenger seat whereas feeling information is not generated in the rear seats. In this case, the display portion 19a of the interface portion 19 shows a display specific to that case where although an occupant is detected in each of place 209 and place 211 schematically representing the right rear seat and the left rear seat, respectively, feeling information of the detected occupant is not generated. This display is hollow circles 225, 227 (a display different from any feeling display and also different from a display shown when an occupant is not detected).

Figure 8:
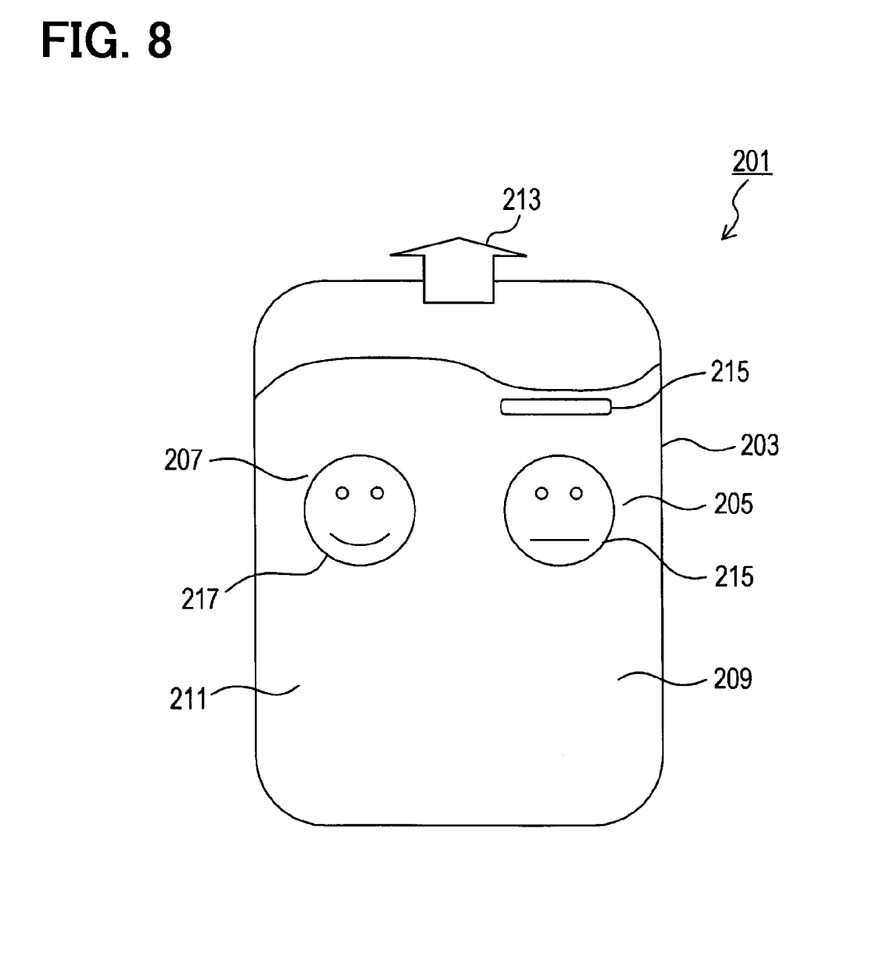
FIG. 8 is an explanatory drawing showing an example of a feeling display.

FIG. 8 shows an example of display shown in a case where an occupant is detected in the driver's seat and the passenger seat and a feeling display of the detected occupant is generated there whereas any occupant is not detected in the rear seats. In this case, the display portion 19a of the interface portion 19 shows nothing in place 209 and place 211 schematically representing the right rear seat and the left rear seat, respectively. (This display is different from any feeling display and also different from hollow circles 225, 227.)

When the feeling display generation section 15 determines that a warning sound should be given off, the interface portion 19 gives off a warning sound through the speaker 19b.

At S7, it is determined whether or not the ignition of the vehicle is on. When it is on, the control proceeds to S1; and when it is off, this series of processing is terminated.

The maps stored in the storage portion 17 can be altered or reset by an occupant inputting his/her voice to the microphone 19c of the interface portion 19 or manipulating the manipulation portion 19d of the interface portion 19. When a map is altered or reset in course of the processing shown in FIG. 2, the processing is aborted and the control returns to S1. Altering and resetting of a map through voice input can be done anytime. Altering and resetting of a map through manipulation with the manipulation portion 19d can be done only when the vehicle is at a stop.

3. Effects Brought about by Feeling Monitoring System 1

(1) When there are multiple occupants in the vehicle, the feeling monitoring system 1 is capable of generating a feeling display representing the feeling of each occupant. For this reason, an occupant can readily become aware of any unusual change in other occupants. Especially, the driver can maintain attention required for driving and grasp how the fellow passengers are.

(2) The feeling monitoring system 1 shows a feeling display in connection with the seating position of the occupant corresponding to the feeling display. For this reason, it is possible to easily understand the correspondence between feeling displays and occupants.

(3) The feeling monitoring system 1 is provided with a map defining a basis pertaining to the type of feeling information and generates a feeling display with respect to feeling information meeting that basis. For this reason, it is possible to generate only feeling displays of high priority. The above-mentioned maps are stored on an occupant-by-occupant basis; therefore, a feeling display to show can be determined according to the condition of each occupant.

(4) The feeling monitoring system 1 is provided with a map defining the correspondence between the intensity of feeling and the mode of feeling display and is capable of varying the mode of feeling display according to the intensity of feeling based on the map. For this reason, it is possible to easily understand the intensity of feeling from a feeling display. Since the above-mentioned maps are stored on an occupant-by-occupant basis, it is possible to determine the mode of feeling display according to the condition of each occupant.

(5) The feeling monitoring system 1 identifies each occupant and uses an applicable map according to the result of the identification. For this reason, even when an occupant changes his/her seating position in mid-course during driving, a map corresponding to that occupant can be used.

4. Other Embodiments (1) For example, the feeling monitoring system 1 may detect only the driver as occupant and give off mechanical synthetic voice (for example, "What's up?") through the speaker 19*b* of the interface portion 19 on condition that: the type of feeling in the feeling information of that driver should be specific and the intensity of feeling be equal to or higher than a predetermined threshold value.

(2) The feeling monitoring system 1 may propose part or all of a feeling improvement section (for example, adjusting air conditioner, adjusting sound level, reproducing music, speaking, and the like) related to an occupant in advance to that occupant or any other occupant. This is done on condition that the type of feeling in the feeling information of the occupant should be specific and the intensity of feeling be equal to or higher than a predetermined threshold value.

(3) Notification may be made (for example, a buzzer sound may be given off from the speaker 19*b* of the interface portion 19) on condition that: feeling information containing a predetermined type of feeling should be acquired from a predetermined proportion or more of detected occupants.

(4) When the camera 3 is installed in each seating position, power to cameras 3 that do not detect an occupant may be turned off.

(5) Detection of an occupant in each seating position may be carried out by a sensor (for example, seat sensor) installed in each seating position.

(6) The feeling monitoring system 1 may be not provided with the interface portion 19. In this case, a signal may be outputted from the feeling display generation section 15 to external equipment (for example, car navigation system, portable terminal, and the like). A feeling display is shown and a notification sound is given off by the external equipment. The display in the external equipment may be identical with that by the display portion 19*a*.

Figure 9:
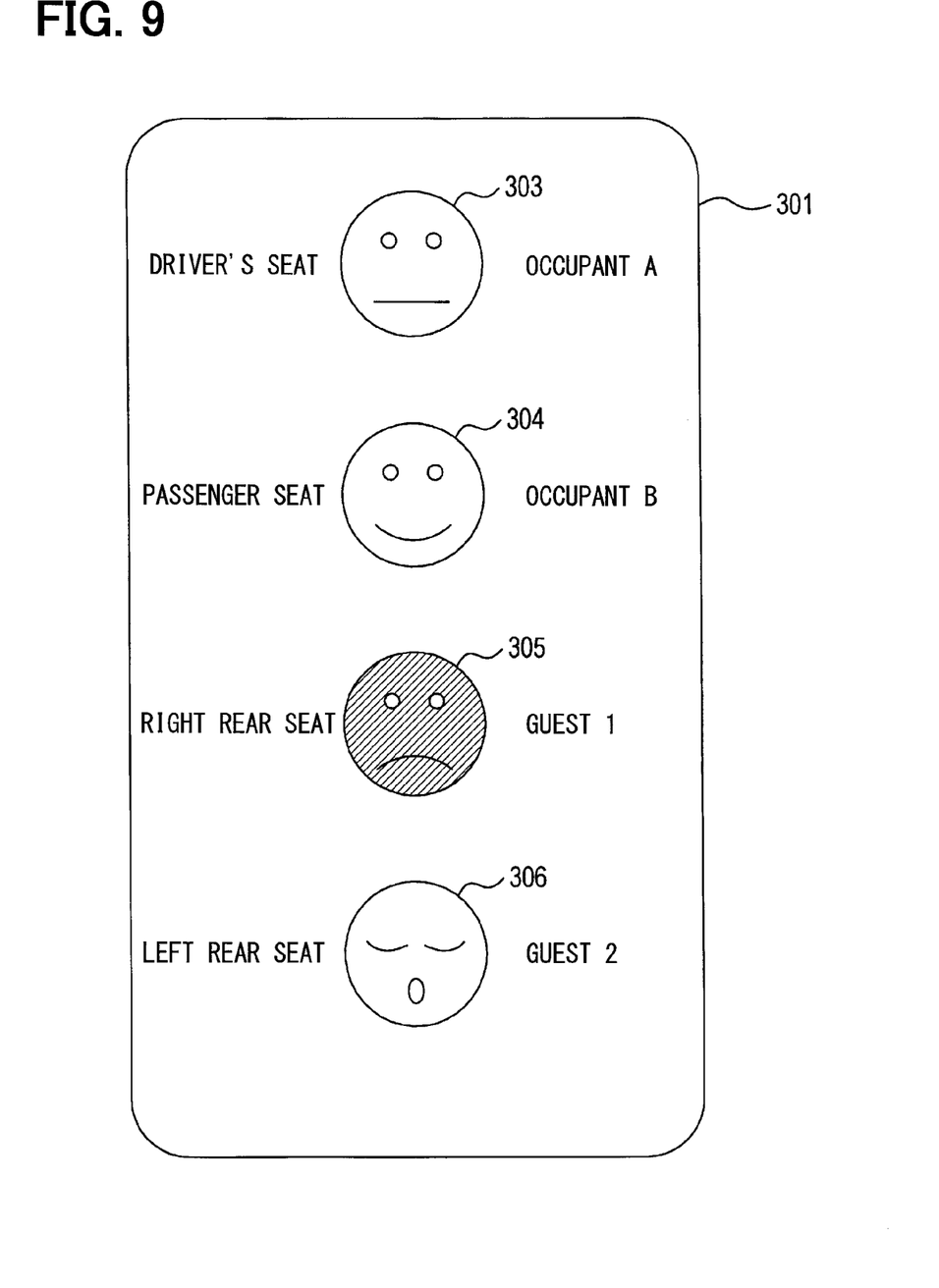
FIG. 9 is an explanatory drawing showing an example of a feeling display.

(7) The mode in which a feeling display is shown in the display portion 19*a* of the interface portion 19 may be as illustrated in FIG. 9. On the left of each feeling display 303, 304, 305, 306, "Driver's seat," "Passenger seat," "Right rear seat," and "Left rear seat" respectively representing the seating position corresponding to each feeling display are indicated. That is, feeling displays 303, 304, 305, 306 are shown in connection with seating positions corresponding to the feeling displays (these seating positions are of occupants whose feeling informations are acquired as the base of the feeling displays).

On the right of feeling displays 303, 304, 305, 306, the names of occupants corresponding to the feeling displays are indicated. More specific description will be given. When at S3, among the identifiers stored in the storage portion 9, there is an identifier identical with or similar to the identifier of the occupant sitting in a seating position, the following processing is carried out: the name of the occupant corresponding to that identifier is indicated on the right of the feeling display. When among the identifiers stored in the storage portion 9, there is not an identifier identical with or similar to the identifier of the occupant sitting in a seating position, "Guest 1," "Guest 2," or the like is indicated.

(8) In the column of "Generation of feeling display" in each map, all the types of feeling may be marked with "O." In this case, feeling displays may be generated based on all the feeling information.

(9) The mode of feeling display may be arbitrarily set. For example, even when the types of feeling are identical, the various modes of feeling display may be varied according to the intensity of feeling. (Examples of the mode of feeling display include the color of feeling display, the luminous intensity of feeling display, the size of feeling display, the motion of feeling display, and the like.) When the intensity of feeling is lower than a predetermined threshold value, a feeling display may be not generated. When the intensity of feeling is lower than a predetermined threshold value, such a display as circles 225, 227 in FIG. 7 may be shown.

(10) Each map may be stored in the storage portion 17 in connection with a seating position. In this case, at S22, a map related to seating position α is read and a feeling display and a notification sound in seating position α are generated using that map. For this reason, a basis pertaining to the type of feeling information and the correspondence between the intensity of feeling and the mode of feeling display are set on a seating position-by-seating position basis.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A feeling monitoring system comprising:
a facial image acquisition portion that acquires a facial image of an occupant individually sitting in each seating position of a plurality of seating positions in a vehicle, the plurality of seating positions including a driver's seat in a front area of the vehicle, a front-passenger seat in the front area of the vehicle, and a rear-passenger seat in a rear area of the vehicle;
a computer configured to:
detect, in a seating position detection section, the seating position of the occupant based on the facial image acquired from the facial image acquisition portion,
acquire, by a feeling information acquisition section, feeling information representing feeling of the occupant based on the facial image acquired from the facial image acquisition portion, and generate, by a feeling display generation section, a feeling display corresponding to the feeling information acquired by the feeling information acquisition section; and a storage portion that stores a plurality of feeling-type bases, wherein feeling-type basis is a basis pertaining to a type of feeling information, the feeling-type basis being previously stored correspondingly for each of the driver's seat, the front-passenger seat, and the rear-passenger seat included in the plurality of seating positions, the feeling-type basis previously stored corresponding for each one of the seating positions is configured to include a plurality of types of feeling, wherein the feeling display generation section:

determines which one of the plurality of feeling-type bases that were previously stored in the storage portion corresponds to the seating position that was detected by the seating position detection section, determines which one of the plurality of types of feeling, included in the feeling-type basis determined to correspond to the seating position that was detected, agrees with the feeling information acquired by the feeling information acquisition section, generates the feeling display that corresponds to the feeling information that is determined to agree with one of the plurality of types of feeling included in the feeling-type basis stored in the storage portion, wherein the feeling-type basis is the one of the plurality of feeling-type bases determined to correspond to a subject seating position detected by the seating position detection section among the plurality of seating positions, responsive to the feeling information acquired by the feeling information acquisition section, when the subject seating position among the plurality of seating positions is detected as the seating position of the occupant by the seating position detection section and the feeling display corresponding to the feeling information of the occupant is generated by the feeling display generation section, the feeling display generation section uses, as the feeling-type basis that corresponds to the feeling information of the occupant, the feeling-type basis previously stored in the storage portion for the subject seating position, as detected by the seating position detection section, of the occupant, the feeling display generation section supports different feeling displays based on identical feeling information for an identical occupant in different seating positions.

2. The feeling monitoring system according to claim 1, wherein the computer is further configured to identify, in an occupant identification section, the occupant individually, wherein the first storage portion stores the basis pertaining to the type of the feeling information specific to the occupant, and wherein the feeling display generation section uses the basis pertaining to the type of the feeling information specific to the occupant based on a result of identification by the occupant identification section.

3. The feeling monitoring system according to claim 1, wherein the storage portion further stores correspondence between an intensity of the feeling and a mode of the feeling display, wherein the feeling information contains the intensity of the feeling, and wherein the feeling display generation section determines the mode of the feeling display generated based on the correspondence between the intensity of the feeling and the mode of the feeling display.

4. The feeling monitoring system according to claim 3, wherein the computer is further configured to identify, in an occupant identification section, the occupant individually, wherein the correspondence stored in the storage portion is specific to the occupant, and wherein the feeling display generation section uses the correspondence specific to the occupant based on a result of identification by the occupant identification section.

5. The feeling monitoring system according to claim 1, wherein the computer is further configured to:

cause a display to display the feeling display in connection with the seating position of the occupant corresponding to the feeling display.

6. The feeling monitoring system according to claim 5, wherein the computer is further configured to identify, in an occupant identification section, the occupant individually, wherein:

the feeling display generation section generates the feeling display corresponding to the feeling information acquired by the feeling information acquisition section based on the occupant identified by the occupant identification section; and the display portion shows the feeling display in connection with the occupant identified by the occupant identification section as well as in connection with the seating position of the occupant identified by the occupant identification section.

7. A feeling monitoring system comprising:

a facial image acquisition portion that acquires a facial image of an occupant individually sitting in each seating position of a plurality of seating positions in a vehicle, the plurality of seating positions including a driver's seat in a front area of the vehicle, a front-passenger seat in the front area of the vehicle, and a rear-passenger seat in a rear area of the vehicle;

a computer configured to detect, in a seating position detection section, the seating position of the occupant based on the facial image acquired by the facial image acquisition portion, acquire, in a feeling information acquisition section, feeling information representing a feeling of the occupant based on the facial image acquired from the facial image acquisition portion, and generate, in a feeling display generation section, a feeling display corresponding to the feeling information acquired by the feeling information acquisition section; and a storage portion that stores a plurality of feeling-intensity-mode correspondences, wherein a feeling-intensity-mode correspondence is a correspondence between (i) a feeling intensity contained in the feeling information and (ii) a feeling-display mode that is a mode of feeling display, the feeling-intensity-mode correspondence being previously stored correspondingly for each of the plurality of seating positions, the feeling-intensity-mode correspondence previously stored corresponding for each one of the seating positions is configured to include correspondence for a plurality of feeling intensities, wherein:

the feeling display generation section determines which one of the plurality of feeling-intensity-mode correspondences that were previously stored in the storage portion corresponds to the seating position that was detected by the seating position detection section, determines which one of the plurality of feeling intensities, included in the feeling-intensity-mode correspondence determined to correspond to the seating position that was detected, agrees with the feeling information acquired by the feeling information acquisition section, generates the feeling display in the feeling-display mode corresponding to the feeling information that is determined to agree with the one of the plurality of feeling intensities included in the feeling-intensity-mode correspondence stored in the storage portion, wherein the feeling-intensity-mode correspondence is the one of the plurality of feeling-intensity-mode correspondences determined to correspond to a subject seating position detected by the seating position detection section among the plurality of seating positions, responsive to the feeling information acquired by the feeling information acquisition section, when the subject seating position among the plurality of seating positions is detected as the seating position of the occupant by the seating position detection section and the feeling display corresponding to the feeling information of the occupant is generated by the feeling display generation section, the feeling display generation section uses, as the feeling-intensity-mode correspondence that corresponds to the feeling information of the occupant, the feeling-intensity-mode correspondence previously stored in the storage portion for the subject seating position, as detected by the seating position detection section, of the occupants, the display generation section supports different feeling displays based on identical feeling information for an identical occupant in different seating positions.

8. The feeling monitoring system according to claim 7, wherein the storage portion further stores a basis pertaining to a type of feeling information, and
wherein the feeling display generation section generates the feeling display with respect to the feeling information agreeing with the basis pertaining to the type of the feeling information.

9. The feeling monitoring system according to claim 8,
wherein the computer is further configured to identify, in an occupant identification section, the occupant individually,
wherein the basis pertaining to the type of the feeling information stored in the storage portion is specific to the occupant, and
wherein the feeling display generation section uses the basis pertaining to the type of the feeling information specific to the occupant based on a result of identification by the occupant identification section.

10. The feeling monitoring system according to claim 7,
wherein the computer is further configured to identify, in an occupant identification section, the occupant individually,
wherein the correspondence stored in the storage portion is specific to the occupant, and
wherein the feeling display generation section uses the correspondence specific to the occupant based on a result of identification by the occupant identification section.

11. The feeling monitoring system according to claim 7, wherein the computer is further configured to:
cause a display to display the feeling display in connection with the seating position of the occupant corresponding to the feeling display.

12. The feeling monitoring system according to claim 11, wherein
the computer is further configured to identify, in an occupant identification section, the occupant individually,
wherein the feeling display generation section generates the feeling display corresponding to the feeling information acquired by the feeling information acquisition section based on the occupant identified by the occupant identification section; and
wherein the display portion shows the feeling display in connection with the occupant identified by the occupant identification section as well as in connection with the seating position of the occupant identified by the occupant identification section.

13. A feeling monitoring method for monitoring feelings of occupants in a vehicle, the vehicle has a plurality of seating positions, comprising:
acquiring, by a facial image acquisition portion, a facial image of an occupant individually sitting in each seating position of a plurality of seating positions in a vehicle, the plurality of seating positions including a driver's seat in a front area of the vehicle, a front-passenger seat in the front area of the vehicle, and a rear-passenger seat in a rear area of the vehicle;
detecting, in a seating position detection section of a computer, the seating position of the occupant based on the facial image acquired from the facial image acquisition portion;
acquiring, by a feeling information acquisition section of the computer, feeling information representing feeling of the occupant based on the facial image acquired from the facial image acquisition portion;
generating, by a feeling display generation section of the computer, a feeling display corresponding to the feeling information acquired by the feeling information acquisition section; and
providing a storage portion that stores a plurality of feeling-type bases, wherein a feeling-type basis is a basis pertaining to a type of feeling information, the feeling-type basis being previously stored corresponding for each of the driver's seat, the front-passenger seat, and the rear-passenger seat included in the plurality of seating positions, the feeling-type basis previously stored correspondingly for each one of the seating positions is configured to include a plurality of types of feeling, wherein
the feeling display generation section:
determines which one of the plurality of feeling-type bases that were previously stored in the storage portion corresponds to the seating position that was detected by the seating position detection section, determines which one of the plurality of types of feeling, included in the feeling-type basis determined to correspond to the seating position that was detected, agrees with the feeling information acquired by the feeling information acquisition section, generates the feeling display that corresponds to the feeling information that is determined to agree with one of the plurality of types of feelings included in the feeling-type basis stored in the storage portion, wherein the feeling-type basis is the one of the plurality of feeling-type bases determined to correspond to a subject seating position detected by the seating position detection section among the plurality of seating positions, responsive to the feeling information acquired by the feeling information acquisition section, when the subject seating position among the plurality of seating positions is detected as the seating position of the occupant by the seating position detection section and the feeling display corresponding to the feeling information of the occupant is generated by the feeling display generation section, the feeling display generation section uses, as the feeling-type basis that the feeling information of the occupant, the feeling-type basis previously stored in the storage portion for the subject seating position, as detected by the seating position detection section, of the occupant, the feeling display generation section supports different feeling displays based on identical feeling information for an identical occupant in different seating positions.

14. The feeling monitoring method according to claim 13, further comprising
identifying, in an occupant identification section, the occupant individually,
wherein the first storage portion stores the basis pertaining to the type of the feeling information specific to the occupant, and
wherein the feeling display generation section uses the basis pertaining to the type of the feeling information specific to the occupant based on a result of identification by the occupant identification section.

15. The feeling monitoring method according to claim 13, wherein the storage portion further stores correspondence between an intensity of the feeling and a mode of the feeling display,
wherein the feeling information contains the intensity of the feeling, and wherein the feeling display generation section determines the mode of the feeling display generated based on the correspondence between the intensity of the feeling and the mode of the feeling display.

16. The feeling monitoring method according to claim 15, further comprising,
identifying, in an occupant identification section of the computer, the occupant individually,
wherein the correspondence stored in the storage portion is specific to the occupant, and
wherein the feeling display generation section uses the correspondence specific to the occupant based on a result of identification by the occupant identification section.

17. The feeling monitoring method according to claim 13, further comprising
causing a display that interfaces to the computer to display the feeling display in connection with the seating position of the occupant corresponding to the feeling display.

18. The feeling monitoring method according to claim 17, further comprising
identifying, in an occupant identification section of the computer, the occupant individually,
wherein:
the feeling display generation section generates the feeling display corresponding to the feeling information acquired by the feeling information acquisition section based on the occupant identified by the occupant identification section; and
the display portion shows the feeling display in connection with the occupant identified by the occupant identification section as well as in connection with the seating position of the occupant identified by the occupant identification section.

19. The feeling monitoring system according to claim 1, wherein the feeling display generation section generates the feeling display which simultaneously represents the feeling information for each of a plurality of occupants which are detected by the seating position detection section in the two or more seating positions in the vehicle.

20. The feeling monitoring system according to claim 7, wherein the feeling display generation section generates the feeling display which simultaneously represents the feeling information for each of a plurality of occupants which are detected by the seating position detection section in the two or more seating positions in the vehicle.

* * * * *